United States Patent
Gilliland et al.

(10) Patent No.: US 11,771,458 B2
(45) Date of Patent: Oct. 3, 2023

(54) ROTARY EMBOLECTOMY DEVICE

(71) Applicants: Charles Gilliland, Atlanta, GA (US); Duc Dao, Lawrenceville, GA (US); Kurt Hickman, Lawrenceville, GA (US); Tanvi Rao, Suwanee, GA (US); Melissa Valdman, Weddington, NC (US)

(72) Inventors: Charles Gilliland, Atlanta, GA (US); Duc Dao, Lawrenceville, GA (US); Kurt Hickman, Lawrenceville, GA (US); Tanvi Rao, Suwanee, GA (US); Melissa Valdman, Weddington, NC (US)

( * ) Notice: Subject to any disclaimer, the term of this patent is extended or adjusted under 35 U.S.C. 154(b) by 231 days.

(21) Appl. No.: 16/772,254

(22) PCT Filed: Dec. 12, 2018

(86) PCT No.: PCT/US2018/065190
§ 371 (c)(1),
(2) Date: Jun. 12, 2020

(87) PCT Pub. No.: WO2019/118586
PCT Pub. Date: Jun. 20, 2019

(65) Prior Publication Data
US 2021/0100581 A1    Apr. 8, 2021

Related U.S. Application Data

(60) Provisional application No. 62/597,761, filed on Dec. 12, 2017.

(51) Int. Cl.
*A61B 17/3207* (2006.01)
*A61B 17/34* (2006.01)
(Continued)

(52) U.S. Cl.
CPC .... *A61B 17/320758* (2013.01); *A61B 17/221* (2013.01); *A61B 17/3423* (2013.01);
(Continued)

(58) Field of Classification Search
CPC ............ A61B 17/12186; A61B 17/221; A61B 17/3207; A61B 17/320758;
(Continued)

(56) References Cited

U.S. PATENT DOCUMENTS 4,589,412 A * 5/1986 Kensey ................. A61B 17/22
606/159
5,267,955 A * 12/1993 Hanson .......... A61B 17/320758
606/171
(Continued)

FOREIGN PATENT DOCUMENTS

CA    2309428 A1 *  5/1995  ........... A61B 17/221

OTHER PUBLICATIONS

Enclose Vocabulary.com Definition, Meaning & Synonyms, https://www.vocabulary.com/dictionary/enclose, accessed Jan. 9, 2023, copyright 2023 Vocabulary.com, Inc. (Year: 2023).*
(Continued)

*Primary Examiner* — Kankindi Rwego
(74) *Attorney, Agent, or Firm* — Meunier Carlin & Curfman LLC

(57) ABSTRACT

Disclosed herein is a rotary embolectomy device. The device includes a rotatable bit which contacts a blood clot within a cannula, thereby disintegrating the clot. The clot can be removed by means of suction, complete disintegration, or a collecting basket.

18 Claims, 7 Drawing Sheets

(51) Int. Cl.
  *A61B 17/00* (2006.01)
  *A61B 17/22* (2006.01)
  *A61B 17/221* (2006.01)

(52) U.S. Cl.
  CPC ........... *A61B 2017/00367* (2013.01); *A61B 2017/00398* (2013.01); *A61B 2017/22084* (2013.01); *A61B 2217/005* (2013.01)

(58) Field of Classification Search
  CPC ...... A61B 17/3423; A61B 2017/00367; A61B 2017/00398; A61B 2017/22038; A61B 2017/22081; A61B 2017/22082; A61B 2017/22084; A61B 2217/005; A61B 2250/0067; A61B 2250/0068; A61B 17/32; A61B 17/32002; A61B 17/320158; A61B 2017/320004; A61B 2017/320008; A61B 2017/320012; A61B 2017/320024; A61B 2017/320028; A61B 2017/320032; A61B 2017/320775; A61B 2017/22068; A61B 2017/22069; A61F 2/013; A61F 2250/0067; A61F 2250/0068
  USPC ........................................................ 606/171
  See application file for complete search history.

(56) References Cited

U.S. PATENT DOCUMENTS

| | | | |
|---|---|---|---|
| 5,376,100 A | 12/1994 | Lefebvre | |
| 5,882,151 A * | 3/1999 | Wirth, Jr. | B23B 49/005 |
| | | | 408/202 |
| 5,925,055 A | 7/1999 | Adrian et al. | |
| 6,719,717 B1 * | 4/2004 | Johnson | A61M 1/34 |
| | | | 604/9 |
| 6,800,083 B2 * | 10/2004 | Hiblar | A61B 17/320758 |
| | | | 606/171 |
| 2001/0018596 A1 | 8/2001 | Selmon et al. | |
| 2002/0099367 A1 * | 7/2002 | Guo | A61B 17/320758 |
| | | | 606/43 |
| 2007/0038226 A1 | 2/2007 | Galdonik et al. | |
| 2011/0208222 A1 | 8/2011 | Ljahnicky et al. | |
| 2014/0296889 A1 | 10/2014 | Avneri et al. | |
| 2017/0224463 A1 * | 8/2017 | Kobayashi | A61B 17/221 |

OTHER PUBLICATIONS

International Search Report and Written Opinion, issued in corresponding application No. PCT/US2018/065190, dated Feb. 27, 2019, 8 pages.

* cited by examiner

ROTARY EMBOLECTOMY DEVICE

CROSS-REFERENCE TO RELATED APPLICATION

This is a national stage application filed under 35 U.S.C. § 371 of PCT/US2018/065190 filed on Dec. 12, 2018, and entitled "Rotary Embolectomy Device," which claims the benefit of U.S. Provisional Application 62/597,761, filed on Dec. 12, 2017, the contents of each are hereby incorporated by reference.

FIELD OF THE INVENTION

The present invention relates to devices and methods for the removal of clots from blood vessels. The invention includes a rotating head which can be used to fragment and disintegrate clot material, which is then removed from the vessel by means of suction. The device can further include a means for delivering a therapeutic agent, for instance to facilitate clot fragmentation.

BACKGROUND

Thrombosis is the formation of a blood clot inside a blood vessel, obstructing the flow of blood through the circulatory system. The formation of a thrombus can occur within the heart or any artery or vein in the body, leading to a myriad of medical problems such as myocardial infarction, stroke, pulmonary embolism, and deep venous thrombosis. Many clinical procedures can result in emboli including, for example, coronary, carotid, and peripheral interventions. In these cases, particulate matter, including, for example, plaque, debris and thrombus, can form emboli distal to the site of intervention. As a result, blood flow to the distal vascular bed can be diminished and periprocedural end-organ ischemia and infarction can result. Distal embolization of large particles produced at the time of such interventions as balloon inflation or stent deployment may obstruct large, epicardial vessels, and smaller particles (as small as 15-100 microns) can cause micro-infarcts and/or myocardial infarctions and left ventricular dysfunction. A significant reason for ischemic injury during percutaneous procedures can be generation of emboli that block smaller distal vessels. One approach to curb this complication has been to use pharmacological therapies during the time of the intervention. However, these therapies, which are often systemically administered, are not without their own complications.

Rapid thrombectomy is frequently needed during the clinical procedures described above in cases of 1) obstruction of arteries of delicate organs, such as the heart or the brain; 2) large clots interrupting blood flow in major vessels or causing severe symptoms; and/or 3) when systemic delivery of the drugs is too risky.

As minimally invasive techniques become more and more prevalent in the medical community, thrombosis and related adverse event are increasing in frequency as well. Multiple thrombectomy devices have emerged in the last decades. However, these devices continue to be largely ineffective against large clot burden, "organized" (i.e. thick) clots, and clots extending from large to small vessels, and many such devices cause distal embolization of clots and vascular damage as they dispose the cutting or macerating mechanism directly into the vascular lumen. In addition, devices are generally specific for a certain lumen size, which translates to the need of combining multiple sizes and types of devices in the same procedure. Mechanical thrombectomy in stroke presents additional challenges based on the tortuosity of vessel and the delicate nature of vessel walls. In this regard, mechanical thrombectomy mechanisms that have been successfully used in the peripheral vasculature to remove clots, some of which are described below, are too bulky and stiff for navigating the complex cerebral artery geometries, release too many clot particles downstream leading to microvascular occlusion, or are too abrasive for delicate brain arterial walls.

There is currently no completely effective method for the uninterrupted removal of blood clots that optimizes the comfort and safety of the patient. One million Americans are annually affected by deep venous thrombosis (DVT). Of these annual DVT cases, 60,000 to 100,000 of diagnoses result in death. Anticoagulants, such as heparin, have been used as the primary therapy for recurrent thrombosis due to their ability to prevent clot formation. However, this therapy is not as effective in older, chronic clots and simultaneously increases the risk of major hemorrhages. Occasionally, stents are used in patients with DVTs. While stents fix the issue, they do not completely remove the blood clot. They also form irregular surfaces on the vessel walls due to a process called endothelialization in which cells grow over the stent. This could present additional problems as it promotes the formation of more clots on the exterior of the stent.

Doctors have increasingly opted for suction embolectomy procedures as the principal means of removing blood clots. The minimally invasive nature of suction embolectomy presents a huge opportunity in the interventional radiology/cardiovascular healthcare space. Unfortunately, all embolectomy devices presently available present fundamental issues. These issues include the following risks: vessel and catheter collapse due to high negative pressure, vessel damage due to traumatic entry, disrupted blood flow due to excess suction or obstruction by catheter, and destruction of blood cells due to high pressure jet with potential to cause kidney failure.

Usability issues for physicians range from mechanical inefficiency to clogging of the device. This clogging frequently occurs because clots can grow without any manifestation of symptoms, and their detection often takes place after they have amassed and matured. As clots mature they harden, presenting an obstacle in the utilization of tissue plasminogen activase (tPA) and suction as mechanisms of removal. Permeating these fibrous clots with tPA, a clot dissolving chemical often utilized in embolectomies, is a challenge, which minimizes the extent of their dissolution. Further, fibrous masses of the clot which are successfully suctioned frequently clog the catheter, which can significantly extend the procedure time. Current suctioning devices must be completely removed, unclogged, cleaned, and reinserted to resume the procedure. Insertion consists of a significant portion of operation time and can be tedious and difficult. The process of removal and reinsertion in minimally invasive procedures like suction embolectomies results in increased operation time and resource utilization as well as increased trauma.

There are currently three known suction embolectomy devices used by physicians. The AngioVac is the largest device (9 mm in diameter) which means it can also be used in larger blood vessels. For the AngioVac, two catheters are placed at two access point on the body and a heart/lung bypass is used to circulate the blood out of and into the body. An external filter is attached in the bypass circuitry to collect the removed clot. The Penumbra is a smaller version of a suction embolectomy device (about 3 mm in diameter) and does not require a heart/lung bypass. The Penumbra is made to be used in smaller vessels and comprises of a wire with a conical tip which can extend in and out of the catheter. This tip is mainly used to dismantle clots at the entrance of the catheter. The AngioVac and Penumbra systems can become defective when large and fibrous clots are lodged inside the catheters. Under this circumstance, the entire system must be removed, and the blood clot has to cleared before resuming the procedure. This presents an inefficiency with the current devices. With the AngioVac, which is much larger and more complex, this can add hours onto the procedure. The AngioJet is another device used in embolectomy procedures. This device utilizes a high velocity tPa jet to physically and chemically eviscerate the clots, which are then inhaled into the catheter due to the negative pressures of the Bernoulli effect. The AngioJet, while fast and effective, has been shown to cause hematuria and kidney failure due to the high pressure jets damaging red blood cells and blood vessels.

Each of the aforementioned devices include a cannula which is inserted into an already placed line. Dislodged and fragmented clot material is then withdrawn through the cannula, however, this material can become trapped within the cannula, thereby reducing the suction power and resulting in incomplete clot removal.

There is a need for improved devices for the efficient removal of clots. There is a need for improved rotational embolectomy devices that can be deployed within a variety of different catheter systems. There is a need for improved rotational embolectomy devices that do not become clogged with dislodged thrombus material. There remains a need for an embolectomy device which can be deployed in a wide variety of different cannulas. There is a need for improved methods to deliver tPA and other agents to clot zones with increased perfusion.

SUMMARY

Disclosed herein are devices for the removal of clots and other obstructions within body lumens, including those of the vasculature system. The devices can fragment, disintegrate, or otherwise dislodge the clot/obstruction from the lumen, and convey the material out of the body without removing the device from the body lumen. The devices include a flexible driveshaft coupled to at least one cutting bit and at least one stabilizer. In contrast with other devices, the inventive devices disclosed herein do not include a separate housing lumen enclosing the flexible driveshaft.

DETAILED DESCRIPTION

Before the present methods and systems are disclosed and described, it is to be understood that the methods and systems are not limited to specific synthetic methods, specific components, or to particular compositions. It is also to be understood that the terminology used herein is for the purpose of describing particular embodiments only and is not intended to be limiting.

As used in the specification and the appended claims, the singular forms "a," "an" and "the" include plural referents unless the context clearly dictates otherwise. Ranges may be expressed herein as from "about" one particular value, and/or to "about" another particular value. When such a range is expressed, another embodiment includes¬ from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

Throughout the description and claims of this specification, the word "comprise" and variations of the word, such as "comprising" and "comprises," means "including but not limited to," and is not intended to exclude, for example, other additives, components, integers or steps. "Exemplary" means "an example of" and is not intended to convey an indication of a preferred or ideal embodiment. "Such as" is not used in a restrictive sense, but for explanatory purposes.

Disclosed are components that can be used to perform the disclosed methods and systems. These and other components are disclosed herein, and it is understood that when combinations, subsets, interactions, groups, etc. of these components are disclosed that while specific reference of each various individual and collective combinations and permutation of these may not be explicitly disclosed, each is specifically contemplated and described herein, for all methods and systems. This applies to all aspects of this application including, but not limited to, steps in disclosed methods. Thus, if there are a variety of additional steps that can be performed it is understood that each of these additional steps can be performed with any specific embodiment or combination of embodiments of the disclosed methods.

Figure 1A:
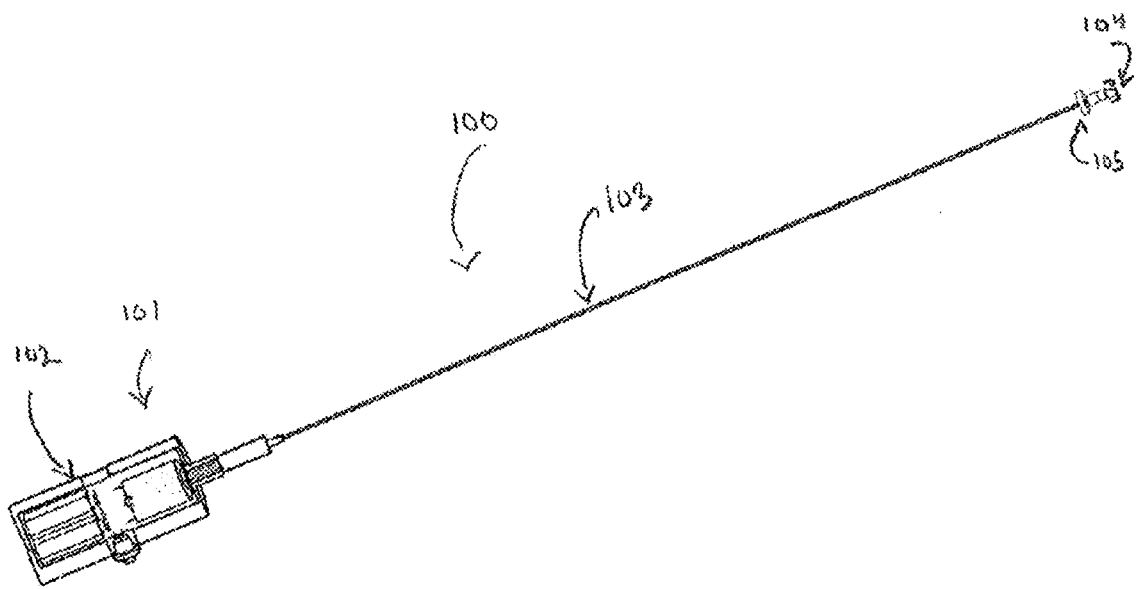
FIG. 1A depicts an embodiment of invention.
Figure 1B:
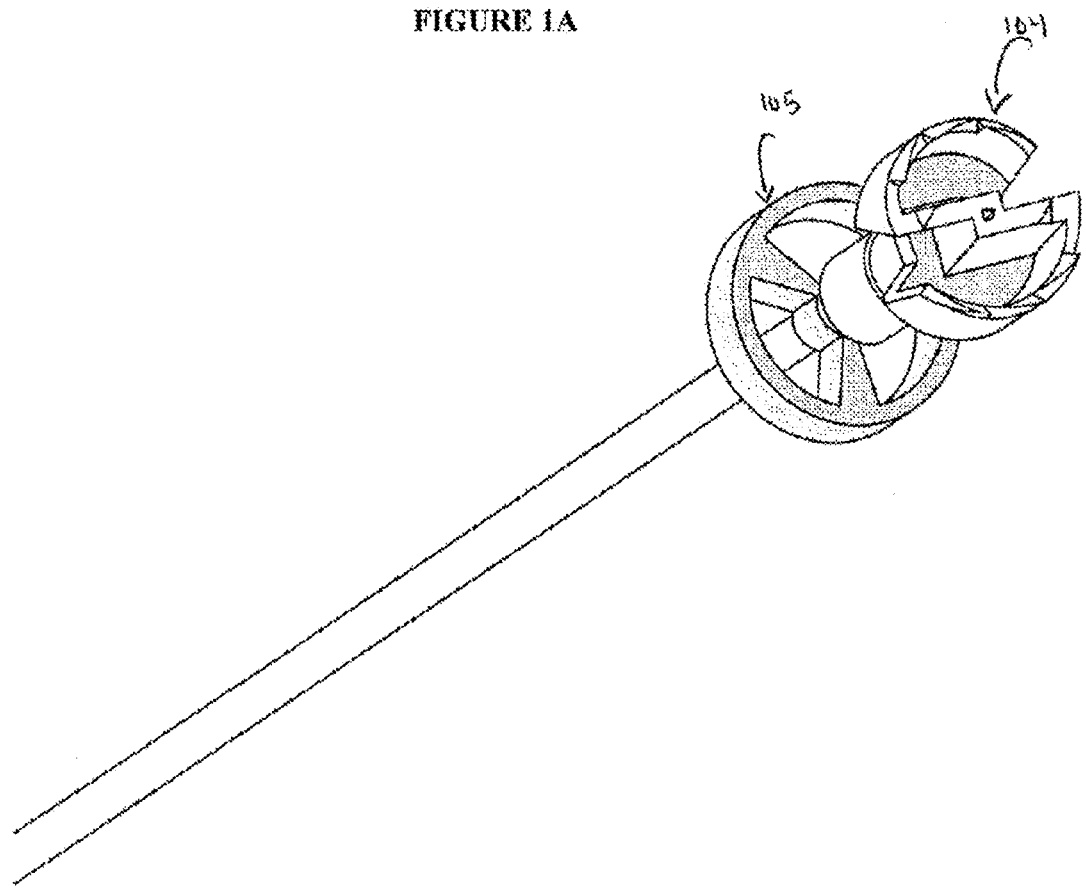
FIG. 1B depicts a rotational shaft, stabilizer, and bit.

Disclosed herein are rotary embolectomy devices which a flexible, rotatable, driveshaft having a proximal end and distal end. With reference to FIGS. 1A and 1B, the device (100) can include proximal end (101) (i.e., closer to the operator) may be coupled with a rotational actuator (102). The distal end (i.e., further from the operator) of the driveshaft (103) includes at least one cutting bit (104) and at least one stabilizer (105). In some embodiments, the device includes a single spacer, while in other embodiments, a plurality (e.g., 2, 3, 4, 5, 6, or more than 6) of spacers are present. The cutting bit does not rotate relative to the driveshaft, such that rotation of the driveshaft rotates the cutting bit as well. In some embodiments, the stabilizer is rotatably coupled to the driveshaft, such that the stabilizer does not rotate when the driveshaft is rotated. In some embodiments, the circumference of the stabilizer (105) is greater than the circumference of the cutting bit (104).

Figure 2:
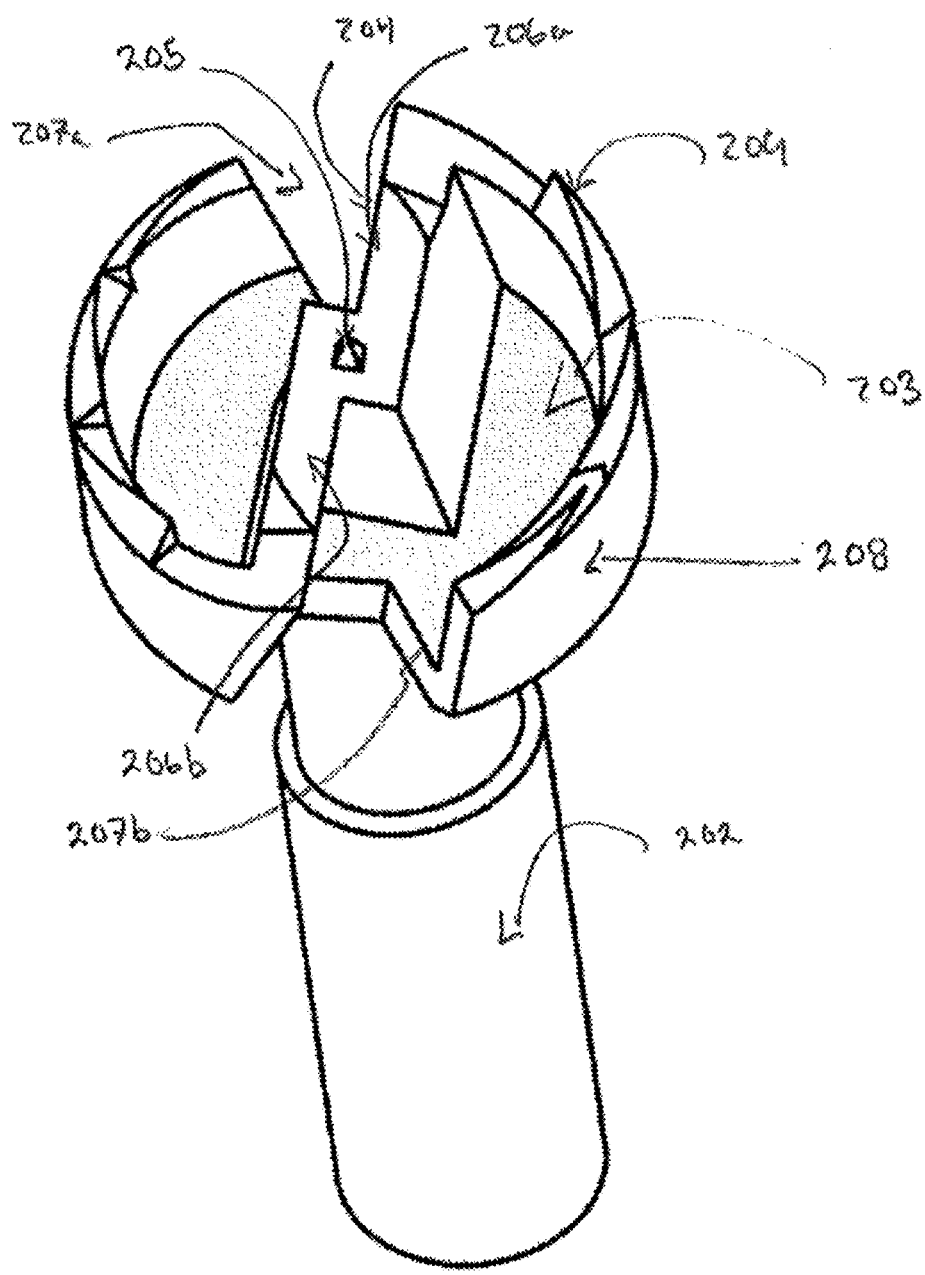
FIG. 2 depicts an embodiment of a Forstner bit.

The cutting bit includes one or more rotatable sharp edges capable of mechanically emulsifying, fragmenting, or disintegrating clots or other blockages. The cutting bit can be contacted with a clot, and the rotating action breaks the clot apart into clot particulates. In some embodiments, the action of the rotating bit will create clot particulates so small that the clot may be considered emulsified. The cutting bit may have a variety of different shapes. In some embodiments, the cutting bit is a Forstner-type bit. With reference to FIG. 2, there is illustrated a Forstner-type bit (201) that includes a central shaft (202) for coupling with the driveshaft, and boring head (203). The circumference of the boring head (203) is greater than the circumference of the central shaft (202). Boring head (203) has a cylindrical configuration and has a main cutting edge (204) extending diametrically across the entire circular cross-section of boring head (203), with a centering point (205). The main cutting edge (204) is interrupted by the centering point (205), such that portion (206*a*) lies adjacent to channel (207*b*) and portion (206*b*) lies adjacent a channel (207*b*) which opens through the outer wall (208) of cutting bit (203) and extends obliquely through the cutting bit (203). Although FIG. 2 depicts an embodiment of a cutting bit having two channels, in other embodiments the cutting head can have one, three, four, or even more channels.

Each outer end of the main cutting edge (204) adjoins a preliminary cutting edge (209) coinciding with the circumference of the boring head (203). Each preliminary cutting edge (209) extends from the end of the main cutting edge (204) around to the edge of the respective other channel (207*a*, 207*b*).

Figure 6:
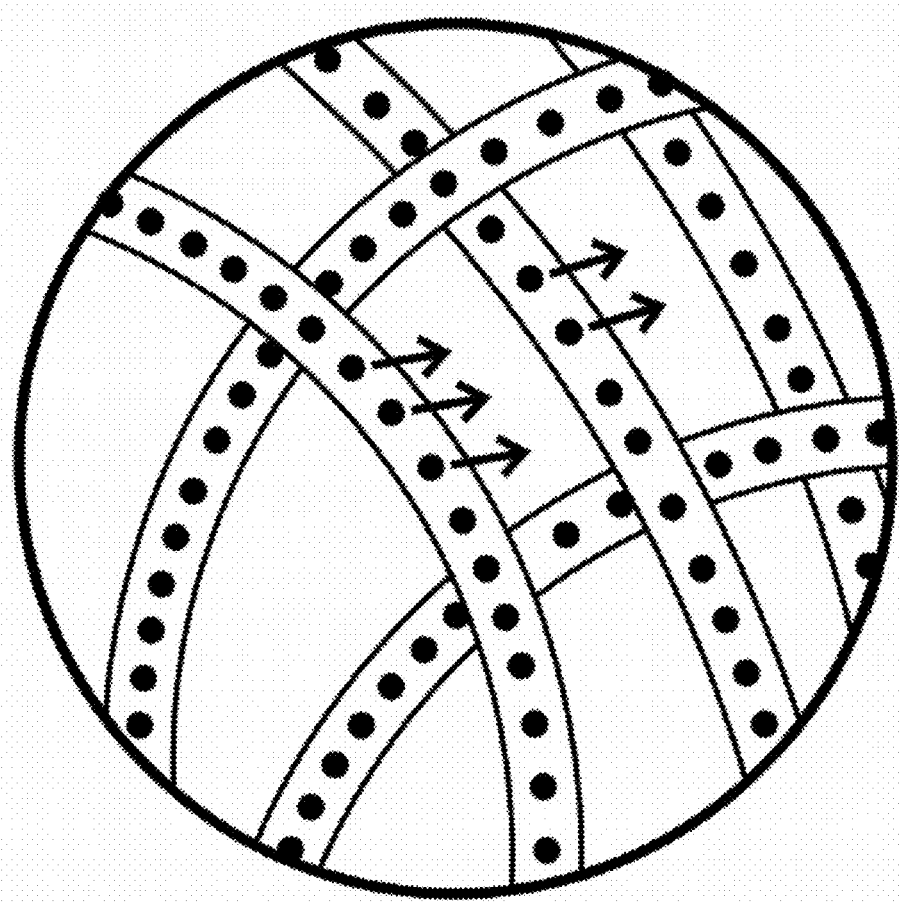
FIG. 6 depicts a dispensing element integrated into a rotary bit as micro-holes, according to an implementation.
Figure 7:
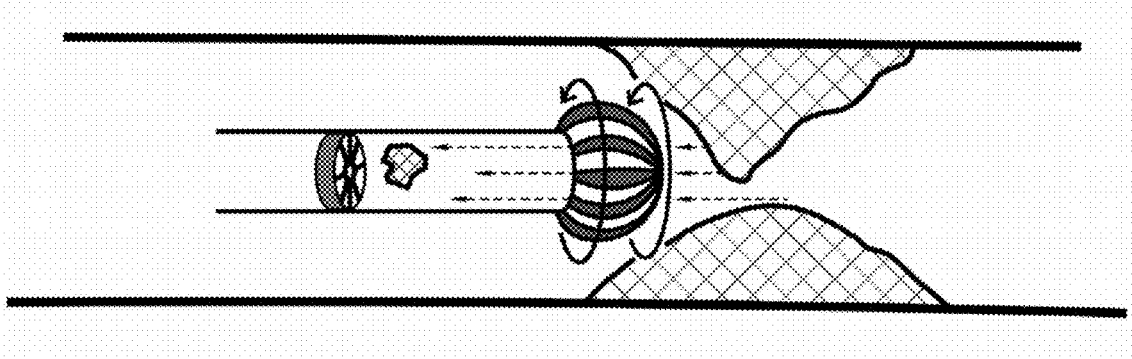
FIG. 7 depicts a threaded cutting head having multiple outlets for delivery of a therapeutic agent.
Figure 8A:
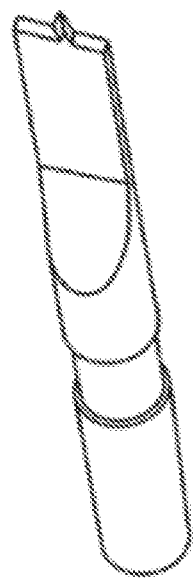
FIG. 8A depicts a bit that can be employed with the invention.
Figure 8B:
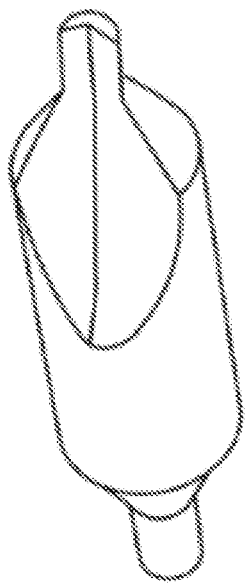
FIG. 8B depicts a bit that can be employed with the invention.
Figure 8C:
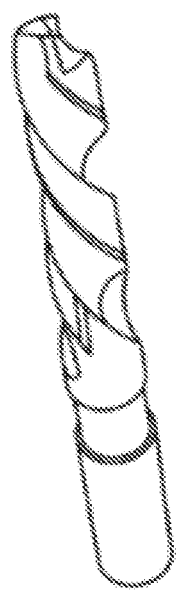
FIG. 8C depicts a bit that can be employed with the invention.
Figure 8D:
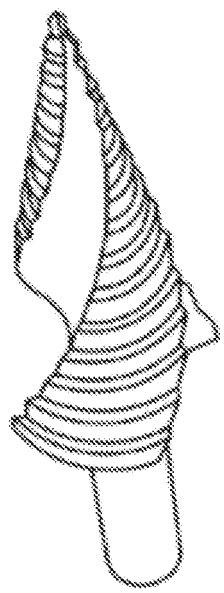
FIG. 8D depicts a bit that can be employed with the invention.

Other cutting bit configurations are depicted in FIG. 8, and include spade bits, twist bits, step bits, and center bits. In certain embodiments, the bit can include a plurality of threaded blades in a basket or fan configuration (FIGS. 6 and 7). The cutting bits disclosed herein may be made of any suitable material that can provide a high level of sharpness and also biocompatibility. Exemplary materials include steel and ceramics. In some instances, additional radiopaque materials may be employed to facilitate visualization of the cutting bit during a procedure.

The cutting bit may be permanently affixed to the driveshaft, or may be reversibly coupled to the driveshaft. When the cutting bit is reversibly coupled, the operator has the option to select the size and type of cutting bit best suited for the need at hand.

Figure 3:
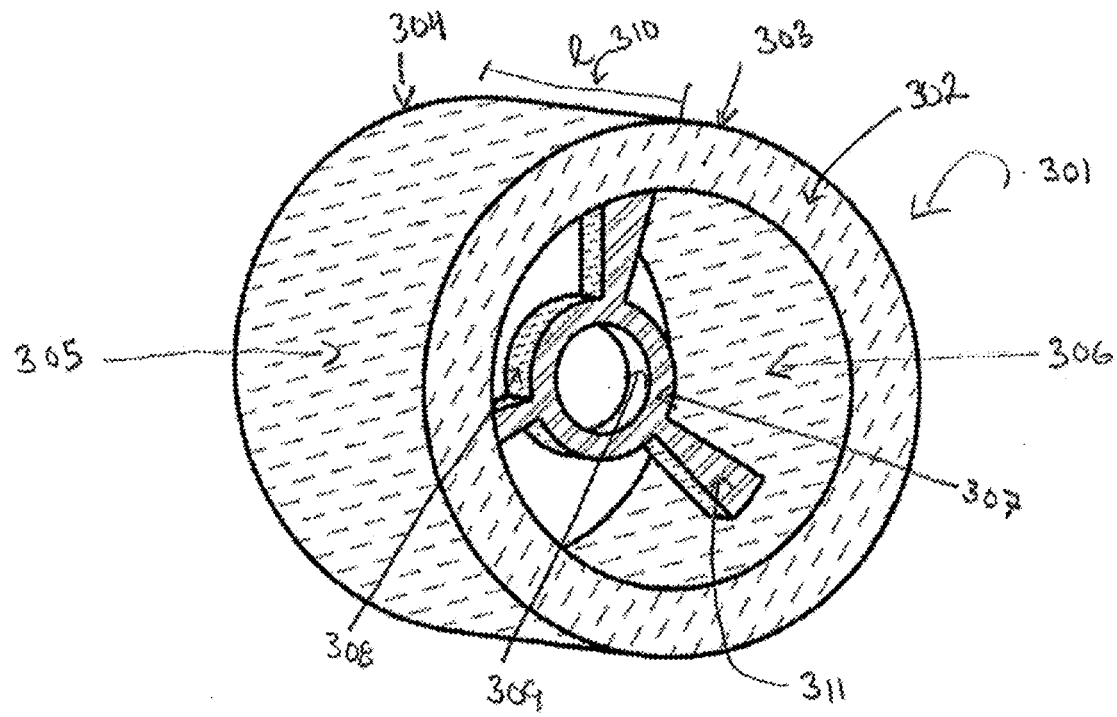
FIG. 3 depicts an embodiment of the stabilizer.
Figure 4:
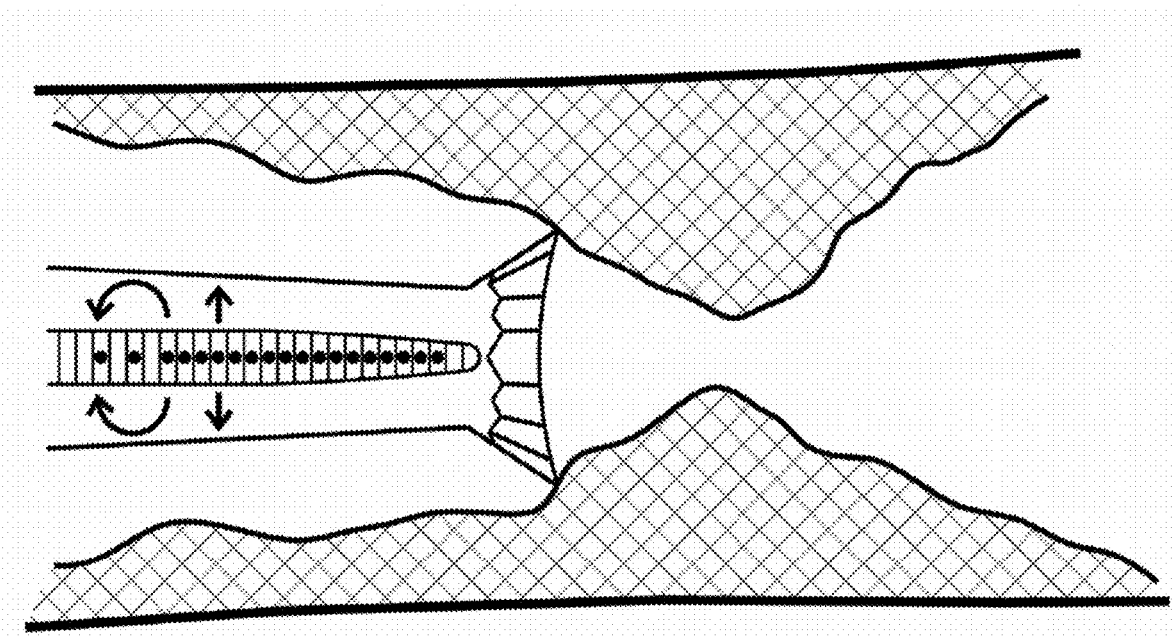
FIG. 4 depicts an embodiment of the invention, including a motor, rotational shaft, stabilizer, and bit.

The stabilizer can include a circular element having an outer diameter that is greater than the outer diameter of the cutting bit. The stabilizer can be made of the same types of material described above for the cutting bit. With reference to FIG. 3, an exemplary stabilizer (301) is described. Stabilizer (301) includes an annular outer portion (302) having a first axial end (303), a second axial end (304) axially spaced apart by length (310) along the axis of the driveshaft, and opposite the first axial end, an outer surface (305) extending between the first and second axial ends, and an inner surface (306) radially opposite and spaced apart from the outer surface of the outer portion. Stabilizer (301) includes an annular inner portion (307) having an outer surface (308) and an inner surface (309) radially opposite and spaced apart from the outer surface of the inner portion. The inner surface (309) defines a loop through which the driveshaft maybe threaded. Stabilizer (301) includes at least one spoke (311) extending radially between the inner surface of the outer portion and the outer surface of the inner portion.

With regard to spoke(s) (309), it is preferred that the spokes take a minimal amount of space relative to the total space between the inner and outer portions. For instance, the spokes can consume no more than 25%, no more than 20%, no more than 15%, no more than 10%, or no more than 5% of the volume between the inner and outer portions.

The driveshaft will be disposed through inner portion (307) of stabilizer (301). The driveshaft can include one or more fixation elements along the shaft to prevent stabilizer (301) from moving along the horizontal axis of the driveshaft. In some embodiments, at least one fixation element is present both proximal and distal to the stabilizer. The fixation element will increase the effective circumference of the driveshaft such that it is greater than circumference of the inner surface (309) of inner portion (307), i.e., the inner circumference of the inner portion. The fixation elements may be permanently attached to the drive shaft, or may be reversibly coupled, such that different stabilizers (for instance, stabilizers having varying outer circumferences) may be affixed to the driveshaft. Fixation elements can be reversibly coupled using quick-change clamps, anchor pins, and the like.

The stabilizer (301) can have a length (310) from the first axial end to the second axial end from about 1-25 mm, from about 2.5-25 mm, from about 2.5-20 mm, from about 5-20 mm, from about 5-15 mm, from about 5-10 mm, from about 7.5-12.5 mm, or from about 10-15 mm. In other embodiments, stabilizer (301) can have a length (310) from the first axial end to the second axial end no more than about 25 mm, no more than about 20 mm, no more than about 15 mm, no more than about 10 mm, no more than about 5 mm, no more than about 2.5 mm, or no more than about 1 mm.

The stabilizer can be spaced apart from the cutting bit by a distance from about 1-25 mm, from about 2.5-25 mm, from about 2.5-20 mm, from about 5-20 mm, from about 5-15 mm, from about 5-10 mm, from about 7.5-12.5 mm, or from about 10-15 mm. For embodiments in which multiple stabilizers are present, the second (and further stabilizers) can be spaced in the proximate direction from the first stabilizer by similar distances. For instance, each subsequent spacer may be spaced apart from the closest distal spacer by a distance from about 1-25 mm, from about 2.5-25 mm, from about 2.5-20 mm, from about 5-20 mm, from about 5-15 mm, from about 5-10 mm, from about 7.5-12.5 mm, or from about 10-15 mm.

The circumference of the outer surface (305) of the annular outer portion (302) will generally be greater than the circumference of the cutting bit. For instance, outer surface (305) can have a circumference that is at least 105%, at least 110%, at least 115%, at least 120%, or at least 125% the circumference of the cutting bit. In certain embodiments, outer surface (305) can have a circumference that is from 100%-125%, from 102.5%-125%, from 102.5%-120%, from 102.5%-115%, from 102.5%-110%, from 102.5%-105%, from 105%-125%, from 105%-120%, from 105%-115%, or from 105%-110% the circumference of the cutting bit. The actual circumference of the stabilizer will depend on the catheter into which it is deployed. Suitable stabilizers can have a circumference slightly less than the catheter. For instance, the stabilizer can have a diameter slightly less than 1 mm, slightly less than 1.35 mm, slightly less than 1.67 mm, slightly less than 2 mm, slightly less than 2.3 mm, slightly less than 2.7 mm, slightly less than 3 mm, slightly less than 3.3 mm, slightly less than 3.7 mm, slightly less than 4 mm, slightly less than 4.3 mm, slightly less than 4.7 mm, slightly less than 5 mm, slightly less than 5.3 mm, slightly less than 5.7 mm, slightly less than 6 mm, slightly less than 6.3 mm, slightly less than 6.7 mm, slightly less than 7.3 mm, slightly less than 8 mm, slightly less than 8.7 mm, slightly less than 9.3 mm, slightly less than 10 mm, slightly less than 10.7 mm, or slightly less than 11.3 mm. As used herein, slightly less refers to a circumference in which the stabilizer can be passed through the catheter, for instance, about 0.5%-20% less, about 1%-20% less, about 1%-10% less, about 1%-5% less, about 2.5%-20% less, about 5%-20% less, or about 10%-20% less.

The device may further include one or more collecting baskets to capture dislodged clot material. The collecting basket may be retractable and can be deployed at the distal end of the catheter proximate to the cutting bit. In some embodiments, the device may be inserted into a catheter, and the collecting funnel deployed. The collecting basket and the device may be withdrawn in a proximal direction and removed from the catheter.

Figure 5:
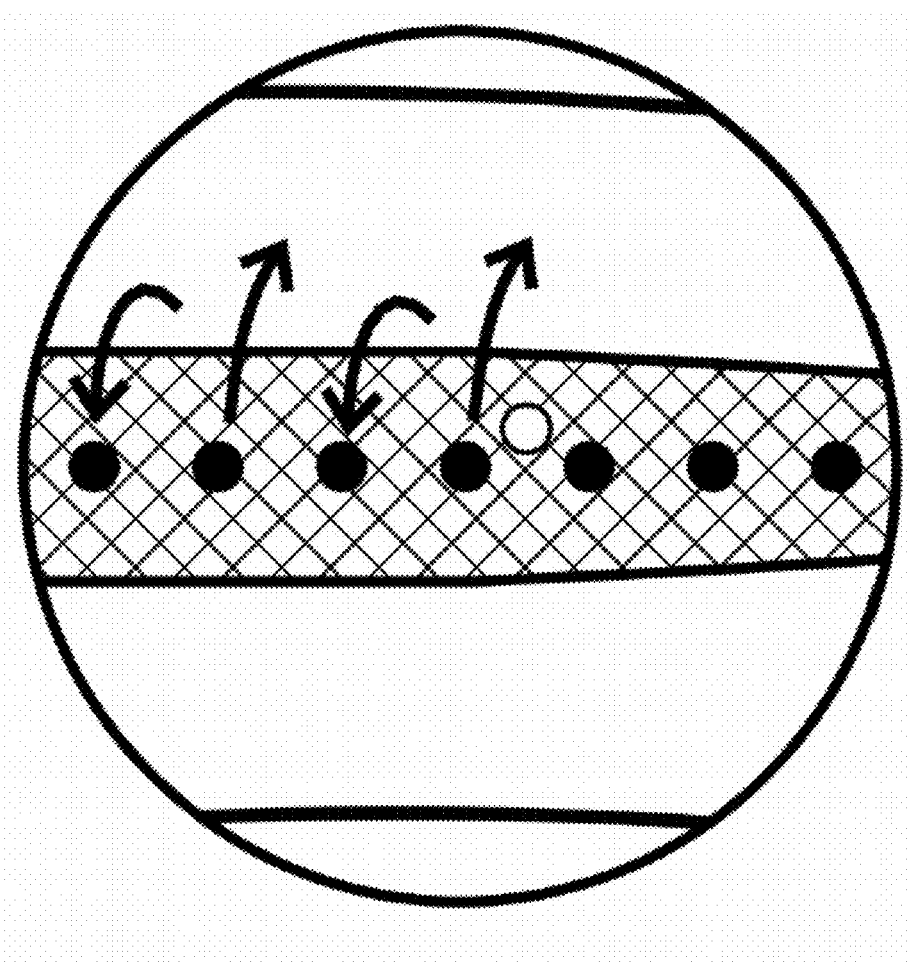
FIG. 5 depicts an embodiment of the invention, including a bit disposed within a cannula, the bit having multiple outlets for delivery of therapeutic agent.

In some embodiments, the device may include one or more dispensing elements for delivery of a solution to the distal end of the device. For instance, the cutting bit and/or stabilizer can include one or more dispensing elements. In some cases, the dispensing element can be integrated into the rotary bit, for instance as micro-holes. (FIGS. 5, 6, and 7). In other embodiments, the dispensing element(s) can be one or more separate needle, tubes, or outlets positioned proximal to the rotary bit (i.e., closer to the operator than the rotary bit). In further embodiments, one or more dispensing elements can be integrated into the stabilizer and/or the collecting basket. The solution can include clot dissolution (lytic) agents such as tissue plasminogen activase, urokinase, streptokinase and tenecteplase; antibiotics; saline, or contrast agents. The solution may be delivered to the distal portion of device via a tube disposed within the driveshaft.

The driveshaft may be coupled to an appropriate actuator for rotating the bit. Exemplary actuators include electric motors and handheld cranks. The actuator provides rotary motion of the driveshaft along the longitudinal axis. The driveshaft may have a length between 25-300 cm, between 25-200 cm, between 50-200 cm, between 75-200 cm, or between 100-200 cm. The driveshaft may be made of a high modulus material with sufficient flexibility and torquability, for instance nitinol, stainless steel, or a composite polymer material. The driveshaft will have a diameter substantially less than the catheter in which it will be deployed.

The devices disclosed herein may be used to remove clots and other blockages (e.g., tumors, infective vegetations, and foreign bodies) in the circulatory system at a site of interest in a variety of contexts, for instance for the treatment of pulmonary embolism, deep vein thrombosis, cerebrovascular embolism, and other types of occlusions. As used herein, the circulatory system includes the cardiopulmonary system and cerebrovascular system. The clots and other bodies may be removed from blood vessels or from one or more chambers of the heart. The device is introduced into an already placed cannula, and the distal end is advanced to the site of interest. The cutting bit is rotated in order to embolize, fragment, or disintegrate the clot. The rotation may be accompanied by administration of one or more agents such as the lytic agents described above, either before, during or after cutting, in other to further disintegrate the clot. Depending on the specific context in which the device is deployed, the clot fragments may be removed by suction, trapping, pharmacologically assisted dissolution or complete emulsification.

In some embodiments the disclosed devices can be deployed in a closed extracorporeal setting. In such embodiments a first cannula, having a distal and proximal end, is provided within a patient, where the distal end is adjacent to the site of interest. The first cannula can be in fluid communication with a pump adapted to provide a sufficient suction force at the site of interest. The inventive devices are introduced into the first cannula by way of an access port, such as a y-connector or similar adaptor, and directed distally towards the end of the first cannula. Upon reaching the clot, the cutting bit is rotated, optionally in combination with administration of a therapeutic agent, including a lytic agent. As the clot is dislodged and disintegrated, the residual material is withdrawn proximally through the first cannula by suction provided by the pump. The first cannula can be in fluid communication with a filter capable of trapping any dislodged material, while the filtered fluid is passed through the filter and collected in a reservoir. The reservoir can include one or more chambers, suitable for oxygenating the fluid, removing carbon dioxide, and adjusting the temperature of the fluid. The reservoir can be in fluid communication with a second cannula, which is also provided within the patient, and which reinfuses the collected fluid back to the patient, optionally by pumping the fluid, from the proximate end of the second cannula (i.e., closer to the reservoir) through the distal end of the second cannula. In some embodiments, the suction and reinfusion are continuously occurring so as to maintain a constant fluid volume within the patient. In other embodiments, the suction and reinfusion are conducted with intermittent pulses. In some embodiments, the pulses alternate between application of suction and reinfusion, while in other embodiments a pulse of both suction and reinfusion is followed by a period in which neither suction nor reinfusion is applied.

The first cannula is not limited as to the locations it may be placed, and the distal end may be directed using conventional techniques to the location of a clot or other blockage anywhere in the body, including a cardiac chamber. The first cannula may be introduced through any suitable vein, for instance the femoral, jugular, or subclavian vein. The distal end of the second cannula may be placed substantially adjacent to the distal end of the first cannula, or may be placed at a different reinfusion site, for instance the femoral vein, iliac vein, inferior vena cava, superior vena cava or right atrium.

Other embodiments do not include reinfusion of filtered fluid by means of the second cannula. In those cases, the dislodged clot can be collected in a basket and the device withdrawn from the cannula. In other instances, the dislodged clot can be completely embolized through the action of the cutting bit, optionally in combination with administration of one or more other lytic agents.

In some embodiments, the devices may be used in the context of a cardiopulmonary bypass. Briefly, in a cardiopulmonary bypass, blood is drained from the right atrium in a patient, by the force of gravity or assisted drainage, oxygenated and filtered, and the returned to the aorta. The embolectomy device may be introduced to the system by means of a y-connector or similar piece, and then advanced to the site of thrombus. The rotating bit fragments the clot, optionally in the presence of added tissue plasminogen activator or other suitable agent, and the resulting debris can be removed by way of an aspiration catheter.

Also provided herein are kits containing the inventive devices. In one embodiment, the kit includes at least one driveshaft, at least one cutting bit, and at least one stabilizer. The kit may further include a solution of lytic agent. In certain embodiments, the kit can include a plurality of stabilizers and bits. For instance, the kit may include one or more of a stabilizer having an outer circumference less than 1 mm, a stabilizer having an outer circumference less than 2 mm, a stabilizer having an outer circumference less than 3 mm, a stabilizer having an outer circumference less than 4 mm, a stabilizer having an outer circumference less than 5 mm, a stabilizer having an outer circumference less than 6 mm, a stabilizer having an outer circumference less than 7 mm, a stabilizer having an outer circumference less than 8 mm, a stabilizer having an outer circumference less than 9 mm, a stabilizer having an outer circumference less than 10 mm, and a stabilizer having an outer circumference less than 11 mm. The kit may further include one or more bits, for instance a Forstner type bit, a spade bit, a twist bit, a step bit, and a center bit. The kit can include multiple Forstner type bits, including a bit having an outer circumference less than 1 mm, a bit having an outer circumference less than 2 mm, a bit having an outer circumference less than 3 mm, a bit having an outer circumference less than 4 mm, a bit having an outer circumference less than 5 mm, a bit having an outer circumference less than 6 mm, a bit having an outer circumference less than 7 mm, a bit having an outer circumference less than 8 mm, a bit having an outer circumference less than 9 mm, a bit having an outer circumference less than 10 mm, and a bit having an outer circumference less than 11 mm. As described earlier, each bit in the kit will have a slightly smaller circumference than the correspondence stabilizer.

The kit may include a driveshaft configured with reversibly coupled fixation devices, so that each of the provided stabilizer and bits may be coupled with the driveshaft.

The compositions and methods of the appended claims are not limited in scope by the specific compositions and methods described herein, which are intended as illustrations of a few aspects of the claims and any compositions and methods that are functionally equivalent are intended to fall within the scope of the claims. Various modifications of the compositions and methods in addition to those shown and described herein are intended to fall within the scope of the appended claims. Further, while only certain representative compositions and method steps disclosed herein are specifically described, other combinations of the compositions and method steps also are intended to fall within the scope of the appended claims, even if not specifically recited. Thus, a combination of steps, elements, components, or constituents may be explicitly mentioned herein or less, however, other combinations of steps, elements, components, and constituents are included, even though not explicitly stated. The term "comprising" and variations thereof as used herein is used synonymously with the term "including" and variations thereof and are open, non-limiting terms. Although the terms "comprising" and "including" have been used herein to describe various embodiments, the terms "consisting essentially of" and "consisting of" can be used in place of "comprising" and "including" to provide for more specific embodiments of the invention and are also disclosed. Other than in the examples, or where otherwise noted, all numbers expressing quantities of ingredients, reaction conditions, and so forth used in the specification and claims are to be understood at the very least, and not as an attempt to limit the application of the doctrine of equivalents to the scope of the claims, to be construed in light of the number of significant digits and ordinary rounding approaches.

What is claimed is:

1. A rotary embolectomy device, comprising:
    a rotatable driveshaft having a distal end and proximal end;
    a cutting bit non-rotatably coupled to or adjacent the distal end of the driveshaft;
    a rotational actuator coupled to or adjacent the proximal end of the driveshaft;
    at least one circular stabilizer rotatably coupled to the driveshaft between the cutting bit and rotational actuator,
    wherein the device does not include a housing lumen enclosing any part of the rotatable driveshaft.

2. The device according to claim 1, wherein an outer circumference of the at least one circular stabilizer is greater than or equal to an outer circumference of the cutting bit.

3. The device according to claim 1, wherein the cutting bit comprises one or more sharp edges.

4. The device according to claim 1, wherein the cutting bit comprises:
    a central shaft non-rotatably coupled to the driveshaft,
    a boring head centered on the central shaft, said boring head having a greater circumference than a circumference of the central shaft;
    an outer wall extending along the circumference of the boring head, said outer wall having one or more channels; and
    a cutting edge extending diametrically across the circular cross-section of the boring head, said cutting edge contacting the outer wall at a location immediately adjacent to the one or more channels.

5. The device according to claim 1, wherein the cutting bit comprises a spade bit, a twist bit, a step bit, or a center bit.

6. The device according to claim 1, wherein the at least one circular stabilizer comprises:
    an annular outer portion comprising an outer surface and an inner surface;
    an annular inner portion comprising an outer surface and an inner surface defining a loop, wherein the driveshaft is disposed through the loop; and
    at least one spoke extending radially between the inner surface of the outer portion and the outer surface of the inner portion.

7. The device according to claim 1, wherein the driveshaft comprises at least one axial stop restricting the movement of the at least one circular stabilizer along the longitudinal axis of the driveshaft.

8. The device according to claim 1, further comprising a dispenser.

9. The device according to claim 1, further comprising a dispenser integrated with the cutting bit.

10. The device according to claim 1, further comprising a dispenser integrated with the at least one circular stabilizer.

11. The device according to claim 1, further comprising a dispenser comprising a tube disposed adjacent to the cutting bit.

12. The device according to claim 1, further comprising a dispenser comprising a tube disposed distal to the cutting bit.

13. The device according to claim 1, wherein the rotatable actuator is an electric motor or a hand crank.

14. A method of removing a blockage in a patient, comprising:
    providing a first cannula disposed within the cerebrovascular system of a patient, said cannula having a distal end adjacent to a blockage, wherein the blockage comprises a clot, and a proximal end comprising an access port;

advancing the distal end of the device according to claim 1 towards the blockage; and rotating the cutting bit to break apart the clot.

15. The method of claim 14, further comprising administering at least one chemical reagent to the blockage.

16. The method of claim 15, wherein the chemical reagent comprises tissue plasminogen activase.

17. The method according to claim 14, wherein the first cannula is in fluid communication with a pump and a filter, and applying suction through the first cannula to withdraw the blockage through the cannula into the filter.

18. The method according to claim 17, wherein the filter is in fluid communication with a reservoir, said reservoir in fluid communication with a second cannula disposed within the patient, comprising the step of reinfusing filtered fluid from the reservoir back into the patient.

\* \* \* \* \*